(12) United States Patent
Umemoto et al.

(10) Patent No.: US 9,789,188 B2
(45) Date of Patent: Oct. 17, 2017

(54) PATCH

(71) Applicant: HISAMITSU PHARMACEUTICAL CO., INC., Tosu-shi (JP)

(72) Inventors: Takuya Umemoto, Tsukuba (JP); Yuka Takagi, Tsukuba (JP); Yasunari Michinaka, Tsukuba (JP)

(73) Assignee: Hisamitsu Pharmaceutical Co., Inc., Tosu-shi (JP)

( * ) Notice: Subject to any disclaimer, the term of this patent is extended or adjusted under 35 U.S.C. 154(b) by 83 days.

(21) Appl. No.: 14/433,939

(22) PCT Filed: Oct. 8, 2013

(86) PCT No.: PCT/JP2013/077328
§ 371 (c)(1),
(2) Date: Apr. 7, 2015

(87) PCT Pub. No.: WO2014/057928
PCT Pub. Date: Apr. 17, 2014

(65) Prior Publication Data
US 2015/0250877 A1    Sep. 10, 2015

(30) Foreign Application Priority Data
Oct. 11, 2012 (JP) .................. 2012-225779

(51) Int. Cl.
*A61K 47/12* (2006.01)
*A61K 31/551* (2006.01)
*A61K 9/70* (2006.01)

(52) U.S. Cl.
CPC ........... *A61K 47/12* (2013.01); *A61K 9/7053* (2013.01); *A61K 9/7061* (2013.01); *A61K 31/551* (2013.01); *A61K 9/7069* (2013.01)

(58) Field of Classification Search
None
See application file for complete search history.

(56) References Cited

U.S. PATENT DOCUMENTS

| | | |
|---|---|---|
| 5,321,022 A | 6/1994 | Nakagawa et al. |
| 5,866,157 A | 2/1999 | Higo et al. |
| 2004/0142024 A1 | 7/2004 | Chono et al. |
| 2007/0184097 A1 | 8/2007 | Kurita et al. |
| 2008/0038328 A1 | 2/2008 | Higo et al. |
| 2009/0169603 A1 | 7/2009 | Iwao et al. |
| 2011/0027365 A1 | 2/2011 | Chono et al. |
| 2014/0037710 A1 | 2/2014 | Hashimoto et al. |

FOREIGN PATENT DOCUMENTS

| | | | |
|---|---|---|---|
| JP | 3 83924 | 4/1991 | |
| JP | 7 33665 | 2/1995 | |
| JP | H0733665 A | * 2/1995 | ............. A61K 31/55 |
| JP | 8 157365 | 6/1996 | |
| JP | 08 193030 | 7/1996 | |
| JP | 11 302161 | 11/1999 | |
| JP | 2007 186500 | 7/2007 | |
| WO | 01 07018 | 2/2001 | |
| WO | 2005 115355 | 12/2005 | |
| WO | 2012 144405 | 10/2012 | |

OTHER PUBLICATIONS

International Search Report Issued Dec. 17, 2013 in PCT/JP13/077328 filed Oct. 8, 2013.

* cited by examiner

*Primary Examiner* — David J Blanchard
*Assistant Examiner* — Daniel F Coughlin
(74) *Attorney, Agent, or Firm* — Oblon, McClelland, Maier & Neustadt, L.L.P.

(57) ABSTRACT

A patch comprising a support layer and an adhesive agent layer, wherein the adhesive agent layer comprises at least one drug selected from the group consisting of emedastine and pharmaceutically acceptable salts thereof, at least one adhesive agent selected from the group consisting of rubber-based adhesive agents and silicone-based adhesive agents, and an alkali metal fumarate as a cohesive force-improving agent for the adhesive agent layer.

22 Claims, 2 Drawing Sheets

PATCH

TECHNICAL FIELD

The present invention relates to a patch, and specifically to a patch comprising emedastine.

BACKGROUND ART

Emedastine is the generic name for 1-(2-ethoxyethyl)-2-(hexahydro-4-methyl-1H-1,4-diazepin-1-yl)-1H-benzimidazole. Emedastine has a histamine release inhibitory action and an antihistaminic action, and is known as a drug which achieves an antiallergic effect. For example, oral preparations such as capsules containing emedastine difumarate (molecular formula: $C_{17}H_{26}N_4O.2C_4H_4O_4$, molecular weight: 534.56) are commercially available.

However, emedastine has the following problem. Specifically, when emedastine administered orally, the emedastine concentration in the blood fluctuates over a wide range, so that adverse effects such as drowsiness tend to be caused. In addition, for example, Japanese Unexamined Patent Application Publication No. Hei 3-83924 (PTL 1) describes parenteral preparations such as oleaginous ointments, gels, creams, lotions, and sprays using a liquid composition comprising emedastine. However, from the viewpoints of reduction of the above-described adverse effects and improvement of the stability of the drug effect, development of a patch which enables more stable continuous administration of emedastine has been desired.

Examples of patches comprising emedastine include a patch comprising an adhesive layer (adhesive agent layer) comprising an acrylic adhesive base, a silicone-based adhesive base or a rubber-based adhesive base, and emedastine described in Japanese Unexamined Patent Application Publication No. Hei 7-33665 (PTL 2), and a patch comprising an adhesive agent layer comprising an acrylic polymer and emedastine described in Japanese Unexamined Patent Application Publication No. Hei 8-193030 (PTL 3).

When an acrylic adhesive agent is used as the adhesive agent, as described in PTLs 2 and 3, somewhat good transdermal absorption of emedastine is exhibited. However, when a rubber-based adhesive agent is used, there arises a problem of insufficient transdermal absorption of emedastine.

In addition, International Publication No. WO2005/115355 (PTL 4) describes a patch comprising an adhesive agent layer comprising a basic drug such as fentanyl or oxybutynin and a volatile organic acid, and also describes various organic acids and organic acid salts including sodium fumarate as compounds which can be added to promote the transdermal absorption of the basic drug, if necessary. However, PTL 4 does not describe emedastine at all.

CITATION LIST

Patent Literature

[PTL 1] Japanese Unexamined Patent Application Publication No. Hei 3-83924
[PTL 2] Japanese Unexamined Patent Application Publication No. Hei 7-33665
[PTL 3] Japanese Unexamined Patent Application Publication No. Hei 8-193030
[PTL 4] International Publication No. WO2005/115355

SUMMARY OF INVENTION

Technical Problem

Moreover, the present inventors have found that when a rubber-based adhesive agent or a silicone-based adhesive agent is used in a conventional patch comprising emedastine, the cohesive force of the adhesive agent layer is so insufficient that there arises such a problem that the adhesive agent layer remains on the skin in the detachment of the patch. In addition, the present inventors have found that the emedastine-release characteristics from the adhesive agent layer deteriorate in a case where emedastine and a rubber-based adhesive agent are simply combined in comparison with cases where other adhesive agents are used, and consequently the transdermal absorption characteristics of emedastine deteriorate.

The present invention has been made in view of the problems of the above-described conventional technologies, and an object of the present invention is to provide a patch excellent in cohesiveness of the adhesive agent layer and in emedastine-release characteristics.

Solution to Problem

The present inventors have conducted intensive study to achieve the above-described object, and consequently have found that when an adhesive agent layer in a patch comprising a support layer and the adhesive agent layer contains a combination of a rubber-based adhesive agent and/or a silicone-based adhesive agent with an alkali metal fumarate, the alkali metal fumarate astonishingly acts as a cohesive force-improving agent for the adhesive agent layer, so that an adhesive agent layer having an excellent cohesiveness can be obtained even when emedastine and/or a pharmaceutically acceptable salt thereof is contained. In addition, the present inventors have also found that such a patch is also excellent in emedastine-release characteristics from the adhesive agent layer, and makes it possible to increase the transdermal absorption of emedastine.

Conventionally, fillers such as titanium oxide, zinc oxide, and silicic acid compounds, plasticizers, and tackifiers are known as additives for improving the cohesive force of the adhesive agent layer, and various compounds as described in PTL 4 are known as additives for promoting the transdermal absorption of drugs. The present inventors have found that both the cohesive force-improving effect and the emedastine-release characteristics-improving effect in the adhesive agent layer can be exhibited by combining emedastine and/or a pharmaceutically acceptable salt thereof, a rubber-based adhesive agent and/or silicone-based adhesive agent, and an alkali metal fumarate with each other. This finding has led to the completion of the present invention.

Specifically, a patch of the present invention comprises a support layer and an adhesive agent layer, wherein the adhesive agent layer comprises at least one drug selected from the group consisting of emedastine and pharmaceutically acceptable salts thereof, at least one adhesive agent selected from the group consisting of rubber-based adhesive agents and silicone-based adhesive agents, and an alkali metal fumarate as a cohesive force-improving agent for the adhesive agent layer.

In the patch of the present invention, the alkali metal fumarate is preferably at least one selected from the group consisting of monosodium fumarate, disodium fumarate, and monopotassium fumarate. Moreover, in the patch of the present invention, a content of the alkali metal fumarate is preferably 1 to 10% by mass in the adhesive agent layer.

Furthermore, in the patch of the present invention, it is preferable that the adhesive agent layer comprise a styrene-based block copolymer or a mixture of a styrene-based block copolymer with polyisobutylene as the adhesive agent, and further comprise liquid paraffin with a mass ratio between the liquid paraffin and the styrene-based block copolymer (a mass of the styrene-based block copolymer/a mass of the liquid paraffin) being less than 1.5.

Advantageous Effects of Invention

The present invention makes it possible to provide a patch excellent in cohesiveness of the adhesive agent layer and in emedastine-release characteristics.

DESCRIPTION OF EMBODIMENTS

Hereinafter, the present invention will be described in detail based on preferred embodiments thereof.

A patch of the present invention comprises a support layer and an adhesive agent layer, wherein the adhesive agent layer comprises at least one drug selected from the group consisting of emedastine and pharmaceutically acceptable salts thereof, at least one adhesive agent selected from the group consisting of rubber-based adhesive agents and silicone-based adhesive agents, and an alkali metal fumarate as a cohesive force-improving agent for the adhesive agent layer.

(Support Layer)

The support layer according to the present invention physically supports the adhesive agent layer, and protects the adhesive agent layer from the external environment. As the support layer, a known support layer for a patch can be employed, as appropriate, without any particular limitation. Examples of materials of such support layers include synthetic resins including polyesters such as polyethylene terephthalate, polybutylene terephthalate, and polyethylene naphthalate; and polyolefins such as polyethylene and polypropylene, and metals such as aluminum. Examples of the forms of such support layers include films; sheets such as foamed sheets and microporous sheets; fabrics such as woven fabrics, knitted fabrics, and nonwoven fabrics; foil; laminates thereof; and the like. Of these materials and forms, a polyester film is preferable, from the viewpoint that it exhibits excellent flexibility and excellent drug-impermeability, when used for a sustained-release patch, which is applied for several days. Meanwhile, a thickness of the support layer is preferably, but not particularly limited to, about 2 to 300 µm, in general.

In addition, the patch of the present invention may have a structure in which the adhesive agent layer is stacked on both surfaces of the support layer, but preferably has a structure in which the adhesive agent layer is stacked on one surface of the support layer, from the viewpoint that such a patch can be produced by a simpler process. In addition, the patch of the present invention more preferably has a structure in which a release liner layer for protecting the adhesive agent layer until the use of the patch is further stacked on the opposite surface of the adhesive agent layer from the support layer.

As the release liner layer, a known release liner layer for a patch can be employed, as appropriate, without any particular limitation. Examples of the release liner layer include films made of a material such as a polyester, polypropylene, polyethylene, or paper, and laminates thereof. The release liner layer is preferably subjected to a release-treatment such as silicone coating to facilitate the detachment. In addition, a thickness of the release liner layer is preferably, but not particularly limited to, about 2 to 300 µm, in general.

(Adhesive Agent Layer)

The adhesive agent layer according to the present invention comprises at least one drug selected from the group consisting of emedastine and pharmaceutically acceptable salts thereof, at least one adhesive agent selected from the group consisting of rubber-based adhesive agents and silicone-based adhesive agents, and an alkali metal fumarate as a cohesive force-improving agent for the adhesive agent layer. A thickness of the adhesive agent layer is preferably, but not particularly limited to, about 20 to 300 µm, in general.

[Drugs]

The adhesive agent layer according to the present invention comprises emedastine as a drug. The emedastine may be a free base, a pharmaceutically acceptable salt of emedastine, or a mixture thereof. The emedastine is preferably contained in the state of a free base in the adhesive agent layer from the viewpoint of further improving the release characteristics from the adhesive agent layer.

Examples of the pharmaceutically acceptable salts of emedastine includes acid addition salts of emedastine, and examples of the acid include monobasic acids such as hydrochloric acid, hydrobromic acid, and methanesulfonic acid; and polybasic acids such as fumaric acid, maleic acid, citric acid, and tartaric acid. Of these acids, fumaric acid is preferable, from the viewpoint that the alkali metal fumarate described later can be formed in the adhesive agent layer, when fumaric acid is contained in the adhesive agent layer in combination with a basic compound containing an alkali metal.

Although a content of emedastine and a pharmaceutically acceptable salt thereof according to the present invention varies depending on the purpose of the treatment, the content is preferably 0.1 to 40% by mass in the adhesive agent layer, in general. In addition, the content is more preferably 0.1 to 20% by mass in the adhesive agent layer, from the viewpoint that the resultant adhesive agent layer has a better cohesiveness and better emedastine-release characteristics.

The adhesive agent layer according to the present invention may further comprise drugs other than emedastine, unless an effect of the present invention is impaired. The drugs are not particularly limited, and examples thereof include antiemetics (examples: granisetron, azasetron, ondansetron, ramosetron, and the like), agents for treating frequent urination due to overactive bladder and the like (examples: oxybutynin, tolterodine, and the like), angiotensin-converting enzyme inhibitors (examples: captopril, delapril, and the like), Ca antagonists (examples: nifedipine and the like), coronary vasodilator (examples: diltiazem, nicorandil, and the like), local anesthetics (examples: lidocaine, procaine, and the like), thymic hormones (examples:

serum thymic factors), muscle relaxants (examples: tizanidine, eperisone, dantrolene, and the like), stimulants, antihypertensive agents (examples: alprenolol, nifedipine, and the like), antitumor agents, psychoactive drugs (examples: imipramine, fentanyl, morphine, and the like), antibiotics, antiparkinsonian drugs (examples: rotigotine, amantadine, levodopa, cocaine, and the like), agents for treating Alzheimer's disease (examples: donepezil, rivastigmine, galantamine, tacrine, memantine, and the like), antihistamines, antivertiginous agents (examples: difenidol, betahistine, and the like), sedative-hypnotic agents, antiinflammatory agents (examples: indomethacin, ketoprofen, diclofenac, and the like), autonomic agents, cardiovascular agents (examples: benzodiazepin and the like), brain metabolic stimulants (examples: vinpocetine and the like), vitamins, polypeptide-based hormones (luteinizing hormone-releasing hormone, thyrotropin-releasing hormone, and the like), peripheral vasodilators, immunomodulatory drugs (examples: polysaccharides, auranofin, lobenzarit, and the like), choleretic drugs (examples: ursodesoxycholic acid and the like), diuretics (examples: hydroflumethiazide and the like), drugs for diabetes mellitus (examples: tolbutamide and the like), agents for treating gout (examples: colchicine and the like), immunosuppressants (examples: tacrolimus, cyclosporine, and the like), and pharmaceutically acceptable salts thereof. One of these drugs may be used alone, or two or more thereof may be used in combination according to the purpose. If any of these drugs other than emedastine is further contained in the adhesive agent layer, a content of these drugs is preferably 0.1 to 40% by mass in the adhesive agent layer, in general, although it varies depending on the purpose of the treatment. The content is more preferably 20% by mass or less in the adhesive agent layer, from the viewpoints that the resultant adhesive agent layer has a better cohesiveness and better emedastine-release characteristics.

[Adhesive Agent]

The adhesive agent layer according to the present invention comprises at least one adhesive agent selected from the group consisting of rubber-based adhesive agents and silicone-based adhesive agents as the adhesive agent. Note that, in the present invention, an adhesive agent refers to a compound which can exhibit tackiness at temperatures (preferably 0° C. to 50° C., more preferably 10° C. to 40° C., and further preferably 15° C. to 40° C.) at which the patch is applied.

Examples of the rubber-based adhesive agents according to the present invention include styrene-based block copolymers such as styrene-isoprene-styrene block copolymer (SIS), styrene-butadiene-styrene block copolymer, and styrene-ethylene.butylene-styrene block copolymer; natural rubber; polyisobutylene (PIB); and polyisoprene. One of these rubber-based adhesive agents may be used alone, or two or more thereof may be used in combination. In addition, of these adhesive agents, the rubber-based adhesive agent according to the present invention is preferably a styrene-based block copolymer or a mixture of a styrene-based block copolymer with polyisobutylene, and more preferably a styrene-isoprene-styrene block copolymer or a mixture of a styrene-isoprene-styrene block copolymer with polyisobutylene, from the viewpoint that both of the cohesive force and the adhesive force of the adhesive agent layer tend to increase. Moreover, the mixture of a styrene-based block copolymer with polyisobutylene preferably has a mass ratio between the styrene-based block copolymer and polyisobutylene (the mass of the styrene-based block copolymer: the mass of polyisobutylene) of 1:5 to 5:1.

In addition, when a styrene-based block copolymer and/or natural rubber is used as the rubber-based adhesive agent, it is preferable to further add at least one selected from the group consisting of tackifiers and softeners described later to the adhesive agent layer, for expression or improvement of the tackiness of the adhesive agent, in general. Note that these tackifiers and softeners may be added, also when other rubber-based adhesive agents or silicone-based adhesive agents described later are used.

When the rubber-based adhesive agent is used as the adhesive agent according to the present invention, a content of the rubber-based adhesive agent is preferably 10 to 99% by mass, and more preferably 15 to 95% by mass in the adhesive agent layer. If the content of the rubber-based adhesive agent is less than the lower limit, the adhesion of the patch to the skin tends to be poor.

As the silicone-based adhesive agent according to the present invention, for example, a polymer having an organopolysiloxane skeleton is preferably used. In addition, when the polymer having an organopolysiloxane skeleton has hydroxyl groups (for example, silanol groups), at least some of the hydroxyl groups are more preferably capped with trimethylsilyl groups. Note that the capping with trimethylsilyl groups includes a mode in which terminal silanol groups of the polymer having an organopolysiloxane skeleton are end-capped with trimethylsilyl groups. Examples of the polymer having an organopolysiloxane skeleton include polydimethylsiloxane (such as a polymer designated as MQ according to ASTM D-1418), polymethylvinylsiloxane (a polymer designated as VMQ according to ASTM D-1418), polymethylphenylsiloxane (a polymer designated as PVMQ according to ASTM D-1418), and the like. One of these polymers may be used alone, or two or more thereof may be used in combination. In addition, as the silicone-based adhesive agent, commercially available ones such as BIO-PSA 7 series (for example, BIO-PSA 7-410X, BIO-PSA 7-420X, BIO-PSA 7-430X) of Dow Corning Corporation, and the like may be used, as appropriate. Of these commercially available silicone-based adhesive agents, BIO-PSA 7-4201 and BIO-PSA 7-4202 are preferable.

When the silicone-based adhesive agent is used as the adhesive agent according to the present invention, a content of the silicone-based adhesive agent is preferably 10 to 99% by mass and more preferably 15 to 95% by mass in the adhesive agent layer. If the content of the silicone-based adhesive agent is less than the lower limit, the adhesion of the patch to the skin tends to be poor.

Note that when a combination of the rubber-based adhesive agent and the silicone-based adhesive agent is used as the adhesive agent according to the present invention, a total content thereof is preferably 10 to 99% by mass, and more preferably 15 to 95% by mass in the adhesive agent layer.

In addition, if necessary, the adhesive agent layer according to the present invention may further comprise other adhesive agents such as acrylic adhesive agents including (meth)acrylic ester copolymers and the like. However, in the present invention, the alkali metal fumarate described later exhibits a function as the cohesive force-improving agent when the rubber-based adhesive agent and/or the silicone-based adhesive agent is used. In addition, from the viewpoint that the cohesive force of the adhesive agent layer tends to decrease when the acrylic adhesive agent is contained in the adhesive agent layer, the content of the other adhesive agents, if contained in the adhesive agent layer according to the present invention, is preferably as follows. Specifically, when the adhesive agent is an acrylic adhesive agent, the content thereof is preferably 10% by mass or less in the adhesive agent layer. It is more preferable that substantially no other adhesive agents be contained.

[Alkali Metal Fumarate]

The present inventors have found the following fact. Specifically, in the present invention, when a combination of the emedastine and/or pharmaceutically acceptable salt thereof, the rubber-based adhesive agent and/or the silicone-based adhesive agent, and an alkali metal fumarate is contained in the adhesive agent layer, the emedastine-release characteristics from the adhesive agent layer are improved, and the alkali metal fumarate functions as the cohesive force-improving agent for the adhesive agent layer, so that the adhesion and cohesiveness of the adhesive agent layer are remarkably improved. Accordingly, the patch of the present invention can be applied more reliably in the application of the patch to the skin of a subject, while the adhesive agent layer left on the skin can be sufficiently reduced in the detachment of the patch.

Examples of the alkali metal fumarate according to the present invention include monosodium fumarate, disodium fumarate, monopotassium fumarate, dipotassium fumarate, and the like. Of these alkali metal fumarates, the alkali metal fumarate is preferably at least one selected from the group consisting of monosodium fumarate, disodium fumarate, and monopotassium fumarate, and more preferably disodium fumarate, from the viewpoint that the cohesiveness and the emedastine-release characteristics of the adhesive agent layer tend to be further improved.

In addition, the alkali metal fumarate according to the present invention may be one added in the form of the compound itself during production, or one produced during production and/or after production and contained in the adhesive agent layer. Examples of methods for causing such an alkali metal fumarate to be contained in the adhesive agent layer include a method in which the alkali metal fumarate according to the present invention, as it is, is added to an adhesive agent layer composition for forming the adhesive agent layer during production of the patch; and a method in which an emedastine salt, emedastine fumarate, is added to the adhesive agent layer composition, and a basic compound containing an alkali metal (an alkali metal hydroxide or the like) is further added as a base corresponding to the emedastine fumarate, so that the emedastine free base and alkali metal fumarate thus formed are contained in the adhesive agent layer.

A content of the alkali metal fumarate according to the present invention is preferably 0.1 to 15% by mass, and more preferably 1 to 10% by mass in the adhesive agent layer. If the content of the alkali metal fumarate is less than the lower limit, the improvement of the cohesiveness of the adhesive agent layer tends to be insufficient. Meanwhile, if the content exceeds the upper limit, problems such as formation of lines tend to be caused during production process. In addition, when the rubber-based adhesive agent is used as the adhesive agent, a content of the alkali metal fumarate is preferably 0.1 to 15% by mass, more preferably 1 to 10% by mass, and further preferably 2 to 5% by mass in the adhesive agent layer. Moreover, when the silicone-based adhesive agent is used as the adhesive agent, the content of the alkali metal fumarate is preferably 0.1 to 15% by mass, more preferably 1 to 10% by mass, and further preferably 3 to 10% by mass in the adhesive agent layer.

[Additives and the Like]

The adhesive agent layer according to the present invention may further comprise additives such as the above-described tackifier, the above-described softener, a solubilizer, a filler, and a stabilizer, unless an effect of the present invention is impaired. Especially when a styrene-based block copolymer and/or natural rubber is used as the adhesive agent, it is preferable that at least one selected from the group consisting of tackifiers and softeners be further contained as described above.

Examples of the tackifiers include rosin resins, rosin ester resins, terpene resins, terpene phenolic resins, C5 petroleum resins, C5/C9 petroleum resins, DCPD (dicyclopentadiene)-based petroleum resins, coumarone.indene resins, alicyclic saturated hydrocarbon resins, and hydrogenated products thereof. One of these tackifiers may be used alone, or two or more thereof may be used in combination. If such a tackifier is contained in the adhesive agent layer, a content of the tackifier is preferably 70% by mass or less in the adhesive agent layer.

Examples of the softeners include petroleum-based oils (examples: paraffinic process oil, naphthenic process oil, aromatic-based process oil, and the like), squalane, squalene, vegetable-based oils (examples: olive oil, camellia oil, castor oil, tall oil, peanut oil, and the like), silicone oils, dibasic acid esters (examples: dibutyl phthalate, dioctyl phthalate, and the like), liquid rubbers (examples: polybutene, liquid isoprene rubber, and the like), liquid fatty acid esters (examples: isopropyl myristate, hexyl laurate, diethyl sebacate, diisopropyl sebacate, and the like), diethylene glycol, polyethylene glycol, glycol salicylate, propylene glycol, dipropylene glycol, triacetin, triethyl citrate, crotamiton, and the like. One of these softeners may be used alone, or two or more thereof may be used in combination. Of these softeners, liquid paraffin, liquid polybutene, isopropyl myristate, diethyl sebacate, and hexyl laurate are preferable, and liquid paraffin is more preferable when the rubber-based adhesive agent is used as the adhesive agent. Meanwhile, a silicone oil is preferable when the silicone-based adhesive agent is used as the adhesive agent. When such a softener is contained in the adhesive agent layer, a content of the softener is preferably 50% by mass or less in the adhesive agent layer.

Although the solubilizer varies depending on the type of the solute to be dissolved, examples of the solubilizer include fatty acids (examples: capric acid, oleic acid, linoleic acid, and the like), fatty acid esters (examples: isopropyl myristate, isopropyl palmitate, and the like), fatty acid derivatives (examples: propylene glycol monolaurate, lauric acid diethanolamide, and the like), fatty acid glycerin esters (examples: glycerin monolaurate, glycerin monooleate, and the like), polyol fatty acid esters (examples: sorbitan monolaurate, and the like), aliphatic alcohols (examples: octyldodecanol, isostearyl alcohol, oleyl alcohol, and the like), polyols (examples: propylene glycol, dipropylene glycol, polyethylene glycol, and the like), pyrrolidone derivatives (examples: N-methyl-2-pyrrolidone and the like), organic acids (examples: acetic acid, lactic acid, and the like), and organic acid salts (examples: sodium acetate, sodium lactate, and the like). One of these solubilizers may be used alone, or two or more thereof may be used in combination. If such a solubilizer is contained in the adhesive agent layer, a content of the solubilizer is preferably 3 to 30% by mass in the adhesive agent layer.

Examples of the filler include inorganic compounds such as silica, aluminum oxide, aluminum hydroxide, zinc oxide, titanium oxide, talc, clay, kaolin, glass, barium sulfate, calcium carbonate, hydroxyapatite, and ceramics; and organic compounds such as cellulose, silk, polyesters, polyolefins, polyacrylic acid esters, polymethacrylic acid esters, and polystyrene. One of these fillers may be used alone, or two or more thereof may be used in combination.

Meanwhile, examples of the stabilizer include tocopherols, ester derivatives of tocopherols, ascorbic acid, ascorbic acid stearate, nordihydroguaiaretic acid, dibutylhydroxytoluene (BHT), butylhydroxyanisole, and the like. One of these stabilizers may be used alone, or two or more thereof may be used in combination. When the filler and/or the stabilizer are contained in the adhesive agent layer, a content of each of the filler and the stabilizer is preferably 30% by mass or less, more preferably 20% by mass or less, and further preferably 10% by mass or less in the adhesive agent layer.

The adhesive agent layer according to the present invention preferably comprises a rubber-based adhesive agent from the viewpoint that the adhesive agent layer exhibits an especially excellent cohesive force-improving effect and an especially excellent emedastine-release characteristics-improving effect in the structure of the present invention. Moreover, it is particularly preferable that a styrene-based block copolymer (preferably a styrene-isoprene-styrene block copolymer) or a mixture of a styrene-based block copolymer (preferably a styrene-isoprene-styrene block copolymer) with polyisobutylene be contained as the rubber-based adhesive agent and that liquid paraffin be contained as the softener. A blending ratio between the rubber-based adhesive agent and the liquid paraffin in this case is preferably less than 1.5, and more preferably 0.5 to 1.25, in terms of the mass ratio between the styrene-based block copolymer and the liquid paraffin (the mass of the styrene-based block copolymer/the mass of the liquid paraffin). If the mass ratio is less than the lower limit, the adhesion of the adhesive agent layer tends to be poor. Meanwhile, if the mass ratio exceeds the upper limit, the resultant adhesive agent layer has somewhat large cohesive force even without having the structure of the present invention, and hence no additional cohesive force-improving effect tends to be exhibited by employing the structure of the present invention.

<Method for Producing Patch>

The patch of the present invention can be produced by a conventionally known method, without any particular limitation. In an example of the method, first, an adhesive agent layer composition is prepared which comprises emedastine and/or a pharmaceutically acceptable salt thereof, the rubber-based adhesive agent and/or the silicone-based adhesive agent, the alkali metal fumarate, a solvent, and, if necessary, the additives. Then, this composition is applied onto one surface of the support layer to a desired thickness, and heated to remove the solvent. Thus, the adhesive agent layer is formed on one surface of the support layer.

The solvent can be selected, as appropriate, according to the types of the drugs, the adhesive agent, and the alkali metal fumarate to be used, and the like, without any particular limitation. Examples of the solvent include lower alcohols such as methanol, ethanol, and isopropanol, toluene, xylene, pentane, n-hexane, cyclohexane, heptane, octane, methyl acetate, ethyl acetate, propyl acetate, methyl butyrate, ethyl butyrate, and propyl butyrate.

In addition, the alkali metal fumarate to be added to the adhesive agent layer composition is preferably ground one. Note that when the alkali metal fumarate is formed during production and/or after production, the use of a composition comprising emedastine fumarate, the rubber-based adhesive agent and/or the silicone-based adhesive agent, a basic compound containing an alkali metal, a solvent, and, if necessary, the additives instead of the above-described adhesive agent layer composition makes it possible to cause the alkali metal fumarate to be contained in the obtained adhesive agent layer.

Moreover, when the patch of the present invention further comprises the above-described release liner layer, the patch of the present invention can be obtained also by, first, applying the adhesive agent layer composition onto one surface of the release liner layer to form the adhesive agent layer, and then stacking the support layer on the opposite surface of the adhesive agent layer from the release liner layer.

EXAMPLES

Hereinafter, the present invention will be described more specifically on the basis of Examples and Comparative Examples. However, the present invention is not limited to Examples below. Note that a cohesiveness evaluation test and a release test in water were conducted on each of the patches obtained in Examples, Comparative Examples, and Reference Examples by the methods described below.

(Cohesiveness Evaluation Test)

First, a piece having a size of 1 cm×5 cm was cut from each of the obtained patches. Then, the release liner layer was detached, and the mass of the patch was measured. After that, the patch was attached to a Bakelite plate, and allowed to stand for 30 minutes. After that, the patch was detached from the Bakelite plate at a rate of 30 cm/min, and the mass of the patch after the detachment was measured. Then, the adhesive agent layer-remaining ratio (%) was calculated by the following formula (1):

The adhesive agent layer-remaining ratio (%)=[(the mass of the patch before the attachment−the mass of the patch after the detachment)/the mass of the patch before the attachment]×100    (1).

Subsequently, from the adhesive agent layer-remaining ratios (%) of a patch (X) prepared by adding an alkali metal fumarate and a patch (Y, standard preparation) prepared in the same manner as in the case of the patch X except that no alkali metal fumarate was added, the cohesive force improvement ratio (%) was calculated by the following formula (2):

The cohesive force improvement ratio (%)={1+[(the adhesive agent layer-remaining ratio of the patch Y−the adhesive agent layer-remaining ratio of the patch X)/the adhesive agent layer-remaining ratio of the patch Y]}×100    (3).

In this evaluation, the cohesive force-improving effect in comparison with the standard preparation was determined to be A, if the cohesive force improvement ratio (%) was 150% or higher, B, if the cohesive force improvement ratio (%) was 110 or higher and lower than 150%, or C, if the cohesive force improvement ratio (%) was less than 110%. Note that when the adhesive agent layer-remaining ratio of the patch Y was 2% or less, the cohesive force-improving effect was determined to be D in this evaluation, irrespective of the value of the cohesive force improvement ratio.

(Release Test in Water)

First, a piece having a size of 2.5 cm×2.5 cm was cut from each of the obtained patches, and the release liner layer was detached. Then, the patch was mounted on a rotatable cylinder of a dissolution tester, with the adhesive agent layer located on the outside. After that, a round-bottom flask to which 900 ml of purified water was added was mounted on the dissolution tester, and the temperature was set to 32° C. Then, the rotatable cylinder was immersed in the purified water in the round-bottom flask. While the rotatable cylinder was rotated at a rate of 50 rpm, a 10 ml eluate sample was collected at predetermined time intervals, and the mass of emedastine released into water (the amount of release in water) was determined by high-performance liquid chromatography, and the total amount of release in water T hours after the start of the measurement (T being any positive number) was found. Then, from the mass of emedastine contained in the adhesive agent layer before the test (initial amount of emedastine), the release ratio (%) in water T hours after the start of the measurement was calculated by the following formula (3):

The release ratio in water (%)=(the total amount of release in water $T$ hours later/the initial amount of emedastine)×100       (3).

Subsequently, the amounts of release in water at all the time points obtained as described above were subjected to curve fitting by the following formula (4) to find the diffusion coefficient ($D_v$ [μm²/hr]) in the pharmaceutical preparation:

[Math. 1]

$$Q(t) = \frac{8C_{v0}L_v}{\pi^2} \sum_{i=1}^{\infty} \frac{1}{(2i-1)^2}\left[1 - \exp\left(-\frac{(2i-1)^2\pi^2 D_v}{4L_v^2}t\right)\right] \quad (4)$$

[in formula (4), $D_v$ represents the diffusion coefficient in the pharmaceutical preparation, $C_{v0}$ represents the initial amount of emedastine, and $L_v$ represents the thickness of the adhesive agent layer]. Note that a greater release ratio in water and/or a greater diffusion coefficient in the pharmaceutical preparation indicates that a larger amount of emedastine is released from the adhesive agent layer, and it can be understood that the transdermal absorption of emedastine is improved by that much.

Reference Example 1

First, 11.9 parts by mass of a styrene-isoprene-styrene block copolymer (SIS, rubber-based adhesive agent), 7.1 parts by mass of polyisobutylene (PIB, rubber-based adhesive agent), 52.3 parts by mass of an alicyclic saturated hydrocarbon resin (ARKON P100, manufactured by Arakawa Chemical Industries, Ltd., tackifier), 23.7 parts by mass of liquid paraffin (softener), and 5 parts by mass of ground disodium fumarate were stirred in toluene to obtain an adhesive agent layer composition. The obtained adhesive agent layer composition was applied onto one surface of a polyethylene terephthalate film (release liner layer) subjected to a release-treatment, and then dried at 80° C. to form an adhesive agent layer having a thickness of 100 μm. Then, a polyethylene terephthalate film (support layer) was stacked on the opposite surface of the adhesive agent layer from the release liner layer. Thus, a patch was obtained.

Reference Examples 2 and 3

Patches of Reference Examples 2 and 3 were obtained in the same manner as in Reference Example 1, except that ground monosodium fumarate (Reference Example 2) or ground monopotassium fumarate (Reference Example 3) was used instead of disodium fumarate. In addition, a patch (standard preparation) not containing any alkali metal fumarate was prepared in the same manner as in Reference Example 1, except that no disodium fumarate was used, and accordingly the amount of each compound added was changed as shown in Table 1. The cohesive force-improving effects in Reference Examples 1 to 3 were evaluated on the basis of comparison with this patch. Table 1 shows the obtained results, together with the constitution (except for toluene) of each of the adhesive agent layer compositions.

TABLE 1

|  |  | Ref. Ex. 1 | Ref. Ex. 2 | Ref. Ex. 3 | Stand. prep. |
| --- | --- | --- | --- | --- | --- |
| Constitution [parts by mass] | SIS | 11.9 | 11.9 | 11.9 | 12.5 |
|  | PIB | 7.1 | 7.1 | 7.1 | 7.5 |
|  | Alicyclic saturated hydrocarbon resin | 52.3 | 52.3 | 52.3 | 55.0 |
|  | Liquid paraffin | 23.7 | 23.7 | 23.7 | 25.0 |
|  | Disodium fumarate | 5.0 | — | — | — |
|  | Monosodium fumarate | — | 5.0 | — | — |
|  | Monopotassium fumarate | — | — | 5.0 | — |
|  | Total amount | 100.0 | 100.0 | 100.0 | 100.0 |
| Evaluation | Cohesive force improvement ratio [%] | 143.3 | 191.8 | 157.9 | — |
|  | Cohesive force-improving effect | B | A | A | — |

Reference Examples 4 to 11

Patches of Reference Examples 4 to 11 were obtained in the same manner as in Reference Example 1, except that the constitution of the adhesive agent layer composition was change to the constitutions shown in Table 2. In addition, for each of the patches of Reference Examples 4 to 11, a patch containing no disodium fumarate was prepared and employed as a standard preparation. Then, the cohesive force-improving effect in each of the patches obtained in Reference Examples 4 to 11 was evaluated on the basis of a comparison with the corresponding standard preparation. Table 2 shows the obtained results, together with the constitution (except for toluene) of each of the adhesive agent layer compositions. Note that the adhesive agent layer remaining ratio of the standard preparation was 2% or less in each of Reference Examples 10 and 11, and hence the evaluation of the cohesive force-improving effect was determined to be D.

TABLE 2

|  |  | Ref. Ex. 4 | Ref. Ex. 5 | Stand. prep. | Ref. Ex. 6 | Stand. prep. | Ref. Ex. 7 | Ref. Ex. 8 | Stand. prep. | Ref. Ex. 9 | Stand. prep. | Ref. Ex. 10 | Ref. Ex. 11 | Stand. prep. |
|---|---|---|---|---|---|---|---|---|---|---|---|---|---|---|
| Constitution [parts by mass] | SIS | 12.2 | 11.3 | 12.5 | 15.2 | 16.0 | 17.1 | 15.7 | 17.5 | 19.7 | 20.8 | 22.1 | 20.3 | 22.5 |
|  | PIB | 7.4 | 6.7 | 7.5 | 7.1 | 7.5 | 7.4 | 6.8 | 7.5 | 7.1 | 7.5 | 7.3 | 6.7 | 7.5 |
|  | Alicyclic saturated hydrocarbon resin | 53.9 | 49.5 | 55.0 | 52.3 | 55.0 | 53.9 | 49.5 | 55.0 | 52.3 | 55.0 | 53.9 | 49.5 | 55.0 |
|  | Liquid paraffin (SIS/Liquid paraffin) | 24.5 | 22.5 0.500 | 25.0 | 20.4 0.750 | 21.5 | 19.6 | 18.0 0.875 | 20.0 | 15.9 1.250 | 16.7 | 14.7 1.500 | 13.5 | 15.0 |
|  | Disodium fumarate | 2.0 | 10.0 | — | 5.0 | — | 2.0 | 10.0 | — | 5.0 | — | 2.0 | 10.0 | — |
|  | Total amount | 100.0 | 100.0 | 100.0 | 100.0 | 100.0 | 100.0 | 100.0 | 100.0 | 100.0 | 100.0 | 100.0 | 100.0 | 100.0 |
| Evaluation | Cohesive force improvement ratio [%] | 182.1 | 171.0 | — | 160.5 | — | 177.3 | 164.1 | — | 197.6 | — | 100.0 | 100.0 | — |
|  | Cohesive force-improving effect | A | A | — | A | — | A | A | — | A | — | D | D | — |

Example 1

First, 16.7 parts by mass of a styrene-isoprene-styrene block copolymer (SIS, rubber-based adhesive agent), 7.1 parts by mass of polyisobutylene (PIB, rubber-based adhesive agent), 52.4 parts by mass of an alicyclic saturated hydrocarbon resin (ARKON P100, manufactured by Arakawa Chemical Industries, Ltd., tackifier), 19.0 parts by mass of liquid paraffin (softener), and 2 parts by mass of ground disodium fumarate were stirred in toluene to obtain a composition comprising the rubber-based adhesive agents. Subsequently, a methanol solution containing 2.8 parts by mass of emedastine (free base) was added to the composition, and the mixture was further stirred to obtain an adhesive agent layer composition. The obtained adhesive agent layer composition was applied onto one surface of a polyethylene terephthalate film (release liner layer) subjected to a release-treatment, and then dried at 80° C. to form an adhesive agent layer having a thickness of 100 μm. Then, a polyethylene terephthalate film (support layer) was stacked on the opposite surface of the adhesive agent layer from the release liner layer. Thus, a patch was obtained.

Examples 2 and 3 and Comparative Example 1

Figure 1:
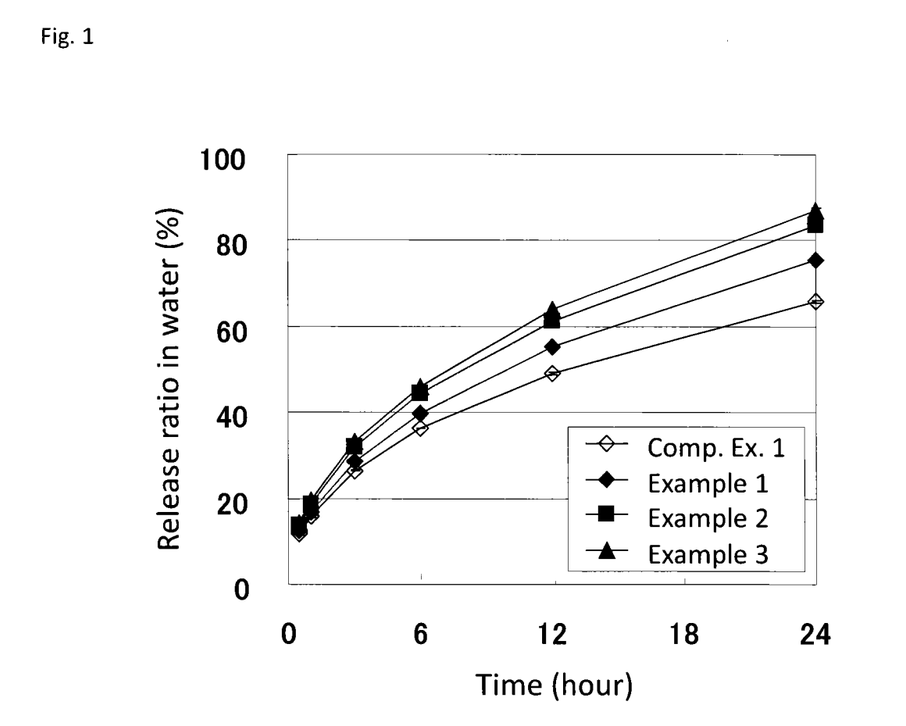
FIG. 1 is a graph showing results of a release test in water conducted on patches obtained in Examples 1 to 3 and Comparative Example 1.

Patches of Examples 2 and 3 were obtained in the same manner as in Example 1, except that 5 parts by mass (Example 2) or 10 parts by mass (Example 3) of disodium fumarate was used, and accordingly the amount of each compound added was changed as shown in Table 3. In addition, a patch (standard preparation) of Comparative Example 1 was obtained in the same manner as in Example 1, except that no disodium fumarate was used, and accordingly the amount of each compound added was changed as shown in Table 3. Subsequently, the cohesiveness evaluation test was conducted on Examples 1 to 3 and Comparative Example 1, and the cohesive force-improving effect in each of the patches obtained in Examples 1 to 3 was evaluated in comparison with the patch (standard preparation) obtained in Comparative Example 1. Table 3 shows the obtained results, together with the constitution (except for toluene and methanol) of each of the adhesive agent layer compositions. In addition, Table 3 and FIG. 1 show the results of the release experiment in water conducted on the patches obtained in Examples 1 to 3 and Comparative Example 1. Note that each release ratio in water in Table 3 is the release ratio in water 24 hours (T=24) after the start of the measurement.

Comparative Example 2

A patch of Comparative Example 2 was obtained in the same manner as in Example 1, except that an adhesive agent layer composition was used which contained an acrylate-based adhesive agent obtained by stirring 95 parts by mass of an acrylate adhesive agent solution (Duro-Tak 87-2516, manufactured by Henkel AG & Co. KGaA) and 5 parts by mass of ground disodium fumarate in toluene. In addition, a patch employed as a standard preparation was prepared in the same manner as described above, except that no disodium fumarate was used, and accordingly the amount of the acrylate adhesive agent solution added was changed to 100 parts by mass. The cohesive force-improving effect in the patch obtained in Comparative Example 2 was evaluated in comparison with the standard preparation. Table 4 shows the obtained results, together with the constitution (except for toluene) of the adhesive agent layer composition.

Comparative Examples 3 to 7

Patches of Comparative Examples 3 to 7 were obtained in the same manner as in Comparative Example 2, except that the constitution of the adhesive agent layer composition was changed as shown in Table 4. In addition, for each of the patches of Comparative Examples 3 to 7, a patch containing no disodium fumarate was prepared and employed as a standard preparation. Then, the cohesive force-improving effect in each of the patches obtained in Comparative Examples 3 to 7 was evaluated in comparison with the corresponding standard preparation. Table 4 shows the obtained results, together with the constitution (except for toluene) of each of the adhesive agent layer compositions. Note that, in Table 4, Duro-Tak 87-2194, Duro-Tak 87-4098, Duro-Tak 87-2051, Duro-Tak 87-202A, and Duro-Tak 87-235A are all acrylate adhesive agent solutions manufactured by Henkel AG & Co. KGaA.

TABLE 3

|  |  | Ex. 1 | Ex. 2 | Ex. 3 | Comp. Ex. 1 (Stand. prep.) |
|---|---|---|---|---|---|
| Constitution [parts by mass] | Emedastine (free base) | 2.8 | 2.8 | 2.8 | 2.8 |
|  | SIS | 16.7 | 16.1 | 15.3 | 17.0 |
|  | PIB | 7.1 | 6.9 | 6.5 | 7.3 |
|  | Alicyclic saturated hydrocarbon resin | 52.4 | 50.7 | 48.0 | 53.5 |
|  | Liquid paraffin | 19.0 | 18.5 | 17.4 | 19.4 |
|  | (SIS/Liquid paraffin) | 0.875 | 0.875 | 0.875 | 0.875 |
|  | Disodium fumarate | 2.0 | 5.0 | 10.0 | — |
|  | Total amount | 100.0 | 100.0 | 100.0 | 100.0 |
| Evaluation | Cohesive force improvement ratio [%] | 174.6 | 196.3 | 189.4 | — |
|  | Cohesive force-improving effect | A | A | A | — |
|  | Release ratio in water (24 hr)[%] | 75.0 | 82.0 | 85.0 | 65.0 |
|  | Diffusion coefficient in pharmaceutical preparation [μm²/hr] | 207.0 | 264.0 | 290.0 | 160.0 |

TABLE 4

|  |  | Comp. Ex. 2 | Stand. prep. | Comp. Ex. 3 | Stand. prep. | Comp. Ex. 4 | Stand. prep. | Comp. Ex. 5 | Stand. prep. | Comp. Ex. 6 | Stand. prep. | Comp. Ex. 7 | Stand. prep. |
|---|---|---|---|---|---|---|---|---|---|---|---|---|---|
| Constitution [parts by mass] | Duro-Tak 87-2516 | 95.0 | 100.0 | — | — | — | — | — | — | — | — | — | — |
|  | Duro-Tak 87-2194 | — | — | — | — | 95.0 | 100.0 | — | — | — | — | — | — |
|  | Duro-Tak 87-4098 | — | — | 95.0 | 100.0 | — | — | — | — | — | — | — | — |
|  | Duro-Tak 87-2051 | — | — | — | — | — | — | 95.0 | 100.0 | — | — | — | — |
|  | Duro-Tak 87-202A | — | — | — | — | — | — | — | — | 95.0 | 100.0 | — | — |
|  | Duro-Tak 87-235A | — | — | — | — | — | — | — | — | — | — | 76.0 | 80.0 |
|  | Isopropyl myristate | — | — | — | — | — | — | — | — | — | — | 19.0 | 20.0 |
|  | Disodium fumarate | 5.0 | — | 5.0 | — | 5.0 | — | 5.0 | — | 5.0 | — | 5.0 | — |
| Evaluation | Total amount | 100.0 | 100.0 | 100.0 | 100.0 | 100.0 | 100.0 | 100.0 | 100.0 | 100.0 | 100.0 | 100.0 | 100.0 |
|  | Cohesive force improvement ratio [%] | 100.0 | — | 100.0 | — | 100.0 | — | 104.0 | — | 105.0 | — | 101.0 | — |
|  | Cohesive force-improving effect | C | — | C | — | C | — | C | — | C | — | C | — |

As is apparent from the results shown in Tables 1 and 2, it has been found that an alkali metal fumarate functions as a cohesive force-improving agent in an adhesive agent layer containing a rubber-based adhesive agent, and an excellent cohesiveness is exhibited in the adhesive agent layer. In addition, as is apparent from the results shown in Tables 3 and 4 and FIG. 1, it has been found that, in the patch of the present invention, an excellent cohesiveness of the adhesive agent layer is exhibited, and the emedastine-release characteristics are also excellent.

In addition, a patch was evaluated which was obtained in the same manner as in Example 1, except that an adhesive agent layer composition was used which was obtained by mixing the composition containing the styrene-isoprene-styrene block copolymer, the polyisobutylene, the alicyclic saturated hydrocarbon resin, the liquid paraffin, and the ground sodium hydroxide with a methanol solution of emedastine difumarate. The obtained results were about the same as the results in Examples 1 to 3.

Example 4

First, 76.3 parts by mass of a silicone-based adhesive agent (BIO-PSA 7-4202, manufactured by Dow Corning Corporation), 17.5 parts by mass of a silicone oil (softener, 350-CST, manufactured by Dow Corning Corporation), and 3.2 parts by mass of ground disodium fumarate were stirred in toluene to obtain a composition containing the silicone-based adhesive agent. Subsequently, a methanol solution containing 3.0 parts by mass of emedastine (free base) was added to the composition, and the mixture was further stirred to obtain an adhesive agent layer composition. The obtained adhesive agent layer composition was applied onto one surface of a polyethylene terephthalate film (release liner layer) subjected to a release-treatment, and then dried at 80° C. for 20 minutes to form an adhesive agent layer having a thickness of 100 μm. Then, a polyethylene terephthalate film (support layer) was stacked on the opposite surface of the adhesive agent layer from the release liner layer. Thus, a patch was obtained.

Examples 5 to 7 and Comparative Example 8

Figure 2:
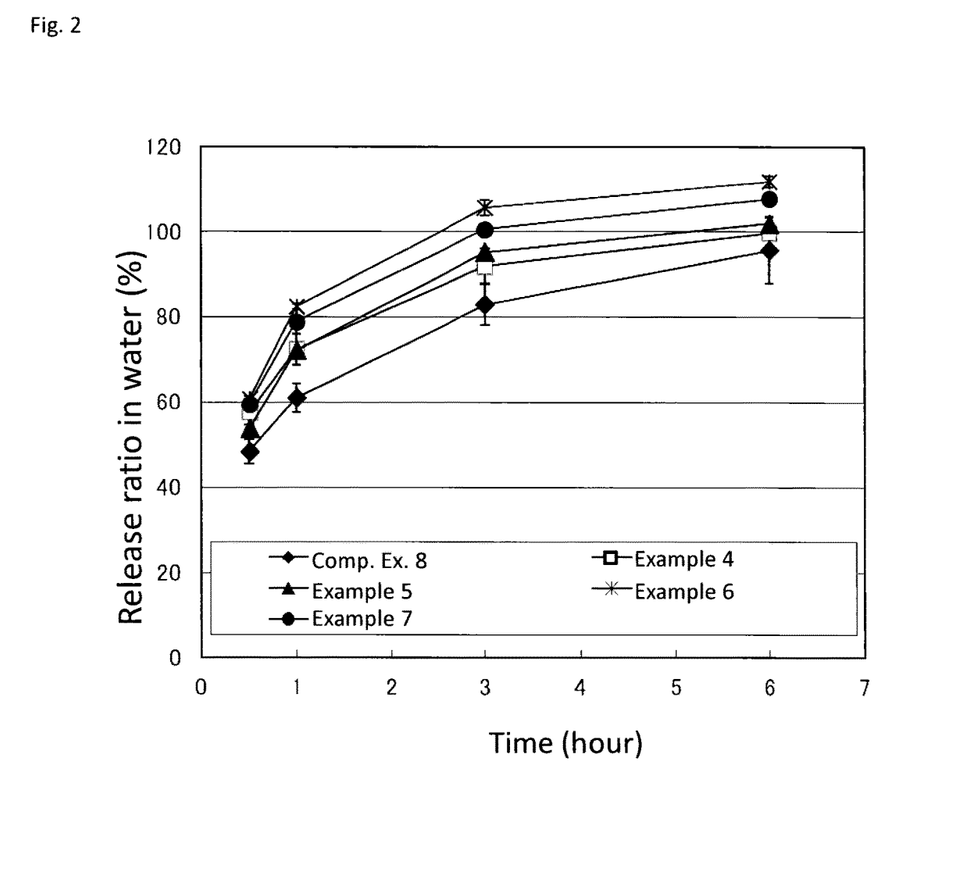
FIG. 2 is a graph showing results of the release test in water conducted on patches obtained in Examples 4 to 7 and Comparative Example 8.

Patches of Examples 5 to 7 were obtained in the same manner as in Example 4, except that 4.0 parts by mass (Example 5), 6.0 parts by mass (Example 6), or 10 parts by mass (Example 7) of disodium fumarate was used, and accordingly the amount of each compound added was changed as shown in Table 5. In addition, a patch (standard preparation) of Comparative Example 8 was obtained in the same manner as in Example 4, except that no disodium fumarate was used, and accordingly the amount of each compound added was changed as shown in Table 5. Subsequently, the cohesiveness evaluation test was conducted on Examples 4 to 7 and Comparative Example 8, and the cohesive force-improving effect in each of the patches obtained in Examples 4 to 7 was evaluated in comparison with the patch (standard preparation) obtained in Comparative Example 8. Table 5 shows the obtained results, together with the constitution (except for toluene and methanol) of each of the adhesive agent layer compositions. In addition, the release experiment in water was conducted on the patches obtained in Examples 4 to 7 and Comparative Example 8. Table 5 and FIG. 2 show the results. Note that, in Table 5, each release ratio in water was the release ratio in water 6 hours (T=6) after the start of the measurement.

TABLE 5

|  |  | Ex. 4 | Ex. 5 | Ex. 6 | Ex. 7 | Comp. Ex. 8 (Stand. prep.) |
|---|---|---|---|---|---|---|
| Constitution [parts by mass] | Emedastine (free base) | 3.0 | 3.0 | 3.0 | 3.0 | 3.0 |
|  | Silicone-based adhesive agent | 76.3 | 75.5 | 73.5 | 69.5 | 79.5 |
|  | Silicone oil | 17.5 | 17.5 | 17.5 | 17.5 | 17.5 |
|  | Disodium fumarate | 3.2 | 4.0 | 6.0 | 10.0 | — |
|  | Total amount | 100.0 | 100.0 | 100.0 | 100.0 | 100.0 |
| Evaluation | Adhesive agent layer-remaining ratio [%] | 36.3 | 33.7 | 22.3 | 14.7 | 51.4 |
|  | Cohesive force improvement ratio [%] | 129.4 | 134.4 | 156.6 | 171.4 | — |
|  | Cohesive force-improving effect | B | B | A | A | — |
|  | Release ratio in water (6 hr) [%] | 100.0 | 102.0 | 112.0 | 108.0 | — |
|  | Diffusion coefficient in pharmaceutical preparation [µm²/hr] | 4196.0 | 4339.0 | 6501.0 | 5617.0 | 2572.0 |

As is apparent from the results shown in Table 5, it has been found that an alkali metal fumarate also functions as a cohesive force-improving agent in an adhesive agent layer containing a silicone-based adhesive agent, and an excellent cohesiveness is exhibited in the adhesive agent layer. In addition, as is apparent from the results shown in Table 5 and FIG. 2, it has been found that, in the patch of the present invention, an excellent cohesiveness of the adhesive agent layer is exhibited, and also the emedastine-release characteristics are excellent.

INDUSTRIAL APPLICABILITY

As described above, the present invention makes it possible to provide a patch excellent in cohesiveness of the adhesive agent layer and in emedastine-release characteristics.

The invention claimed is:

1. A patch, comprising:
a support layer; and
an adhesive agent layer,
wherein the adhesive agent layer comprises emedastine and or a pharmaceutically acceptable salt thereof, a rubber-based adhesive agent and/or a silicone-based adhesive agent, and disodium fumarate.

2. The patch according to claim 1, further comprising monosodium fumarate and/or monopotassium fumarate.

3. The patch according to claim 1, wherein a content of the disodium fumarate is 1 to 10% by mass in the adhesive agent layer.

4. The patch according to claim 1, wherein the adhesive agent layer comprises a styrene-based block copolymer or a mixture of a styrene-based block copolymer with polyisobutylene, and further comprises a liquid paraffin with a mass ratio of less than 1.5 between the liquid paraffin and the styrene-based block copolymer.

5. The patch according to claim 1, wherein the adhesive agent layer comprises the emedastine.

6. The patch according to claim 1, wherein the adhesive agent layer comprises the pharmaceutically acceptable salt of emedastine.

7. The patch according to claim 1, wherein the adhesive agent layer comprises the rubber-based adhesive agent.

8. The patch according to claim 1, wherein the adhesive agent layer comprises the silicon-based adhesive agent.

9. The patch according to claim 1, further comprising monosodium fumarate.

10. The patch according to claim 1, further comprising monopotassium fumarate.

11. The patch according to claim 3, wherein the adhesive agent layer comprises a styrene-based block copolymer or a mixture of a styrene-based block copolymer with polyisobutylene, and further comprises a liquid paraffin with a mass ratio of less than 1.5 between the liquid paraffin and the styrene-based block copolymer.

12. The patch according to claim 3, wherein the adhesive agent layer comprises the emedastine.

13. The patch according to claim 3, wherein the adhesive agent layer comprises the pharmaceutically acceptable salt of emedastine.

14. The patch according to claim 1, wherein the adhesive agent layer comprises the rubber-based adhesive agent.

15. The patch according to claim 1, wherein the adhesive agent layer comprises the silicon-based adhesive agent.

16. The patch according to claim 3, wherein the adhesive agent layer comprises the rubber-based adhesive agent.

17. The patch according to claim 3, wherein the adhesive agent layer comprises the silicon-based adhesive agent.

18. The patch according to claim 1, wherein the adhesive agent layer comprises the emedastine and the rubber-based adhesive agent.

19. The patch according to claim 18, wherein the adhesive agent layer comprises a styrene-based block copolymer or a mixture of a styrene-based block copolymer with polyisobutylene, and further comprises a liquid paraffin with a mass ratio of less than 1.5 between the liquid paraffin and the styrene-based block copolymer.

20. The patch according to claim 3, wherein the adhesive agent layer comprises the emedastine and the rubber-based adhesive agent.

21. The patch according to claim 20, wherein the adhesive agent layer comprises a styrene-based block copolymer or a mixture of a styrene-based block copolymer with polyisobutylene, and further comprises a liquid paraffin with a mass ratio of less than 1.5 between the liquid paraffin and the styrene-based block copolymer.

22. The patch according to claim 2, wherein the adhesive agent layer comprises a styrene-based block copolymer or a mixture of a styrene-based block copolymer with polyisobutylene, and further comprises a liquid paraffin with a mass ratio of less than 1.5 between the liquid paraffin and the styrene-based block copolymer.

* * * * *